United States Patent
Woods et al.

(10) Patent No.: US 8,274,298 B2
(45) Date of Patent: Sep. 25, 2012

(54) CALIBRATION STRUCTURE FOR FLEX FUEL SENSOR

(75) Inventors: Ralf Woods, Clarkston, MI (US); David VanZuilen, Fremont, IN (US); Thomas Nodine, Goshen, IN (US)

(73) Assignee: Continental Automotive Systems US, Inc., Auburn Hills, MI (US)

( * ) Notice: Subject to any disclaimer, the term of this patent is extended or adjusted under 35 U.S.C. 154(b) by 395 days.

(21) Appl. No.: 12/615,287

(22) Filed: Nov. 10, 2009

(65) Prior Publication Data

US 2011/0109323 A1    May 12, 2011

(51) Int. Cl.
*G01R 35/00*    (2006.01)
(52) U.S. Cl. .......................................................... 324/601
(58) Field of Classification Search ..................... 324/601
See application file for complete search history.

(56) References Cited

U.S. PATENT DOCUMENTS

| | | | |
|---|---|---|---|
| 3,781,673 A * | 12/1973 | Resh | 324/689 |
| 4,724,382 A * | 2/1988 | Schauerte | 324/133 |
| 5,627,304 A * | 5/1997 | Jacob et al. | 73/1.73 |
| 6,803,766 B2 * | 10/2004 | Kobayashi et al. | 324/434 |
| 6,842,017 B2 | 1/2005 | McKenzie et al. | |
| 6,885,199 B2 | 4/2005 | Desmier et al. | |
| 6,927,583 B2 | 8/2005 | Vanzuilen et al. | |
| 7,135,870 B2 | 11/2006 | Mohajer | |
| 7,170,303 B2 | 1/2007 | Vanzullen et al. | |
| 2003/0016064 A1 * | 1/2003 | Hartmann et al. | 327/172 |
| 2009/0113981 A1 * | 5/2009 | Beer | 73/1.02 |
| 2009/0288964 A1 * | 11/2009 | Jung et al. | 205/792 |

* cited by examiner

*Primary Examiner* — Jeff Natalini

(57) ABSTRACT

A calibration structure (10) for calibrating a flex fuel sensor (12) for a vehicle is provided. The flex fuel sensor has a first sensor electrode (14) and a second sensor electrode (16). The calibration structure includes a first electrode (30), a second electrode (36) spaced from and electrically insulated from the first electrode, and at least one capacitor (40), or at least one resistor (42), or at least one combination of a capacitor with a resistor, of a certain value electrically connected with the first and second electrodes. The first electrode (30) is constructed and arranged to contact the first sensor electrode (16) and the second electrode (36) is constructed and arranged to contact the second sensor electrode (14) to provide a known input value to the flex fuel sensor for calibration of the flex fuel sensor without the use of test liquids.

20 Claims, 2 Drawing Sheets

CALIBRATION STRUCTURE FOR FLEX FUEL SENSOR

FIELD

The embodiment relates to a probe for calibrating a flex fuel sensor of a vehicle without using fuels or test liquids during the calibration process.

BACKGROUND

A typical flex fuel sensor used in a flex fuel vehicle operates by sampling the capacitance, conductance, and temperature of a given fuel. The sensor outputs the value of the fuel to an electronic engine controller which, along with other inputs, adjusts the fuel air ratio accordingly to make the vehicle's engine run properly.

In the process of manufacturing a flex fuel sensor, a calibration process must be performed to offset minor errors in manufacturing tolerance. In the past, this process was done employing a combination of fuels used in the application. Obviously, this poses a safety problem in the manufacturing environment with a potential fire hazard and forces the manufacturing plant to manage a potentially hazardous material. Subsequently, these fuels were replaced with less volatile test liquids having the same capacitance and conductance as the fuels. However, a problem still exists using a combination of liquids, keeping the concentrations correct, and successfully removing the liquid from the sensor prior to shipment.

Thus, there is a need to provide structure for calibrating a flex fuel sensor without the need to use fuel or other liquids during the calibration.

SUMMARY

An object of the present invention is to fulfill the need referred to above. In accordance with the principles of an embodiment, this objective is obtained by providing a calibration structure for calibrating a flex fuel sensor for a vehicle. The flex fuel sensor has a first sensor electrode and a second sensor electrode. The calibration structure includes a first electrode, a second electrode spaced from and electrically insulated from the first electrode, and at least one capacitor, or at least one resistor, or at least one combination of a capacitor with a resistor, of a certain value electrically connected with the first and second electrodes. The first electrode is constructed and arranged to contact the first sensor electrode and the second electrode is constructed and arranged to contact the second sensor electrode to provide a known input value to the flex fuel sensor for calibration of the flex fuel sensor without the use of test liquids.

In accordance with another aspect of the embodiment, a method is provided for calibrating a flex fuel sensor for a vehicle. The flex fuel sensor has a first sensor electrode and a second sensor electrode. The method provides a calibration structure comprising a first electrode, a second electrode spaced from and electrically insulated from the first electrode, and at least one capacitor, or at least one a resistor, or at least one combination of a capacitor with a resistor, of a certain value electrically connected with the first and second electrodes. The first electrode electrically contacts the first sensor electrode and the second electrode electrically contacts the second sensor electrode thereby providing a known input value to the fuel flex sensor for use in calibrating the fuel flex sensor absent the use of test liquids.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF AN EXAMPLE EMBODIMENT

Figure 1:
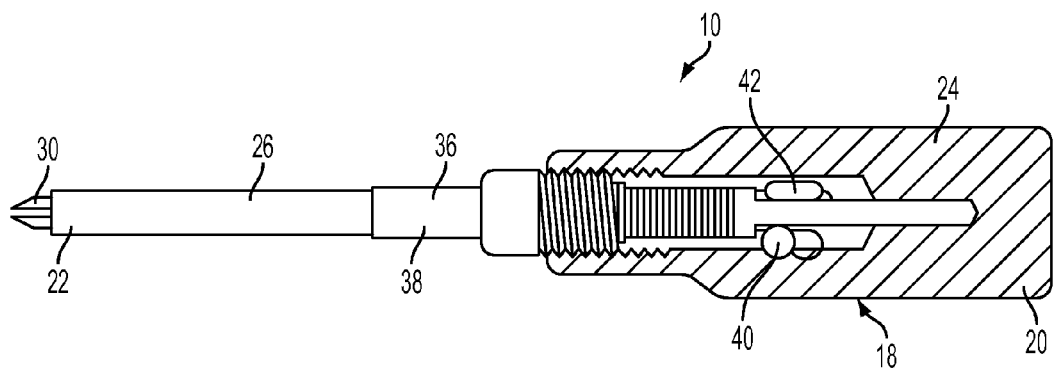
FIG. 1 is a view of a calibration structure, shown partially in section, in accordance with an embodiment of the present invention.
Figure 2:
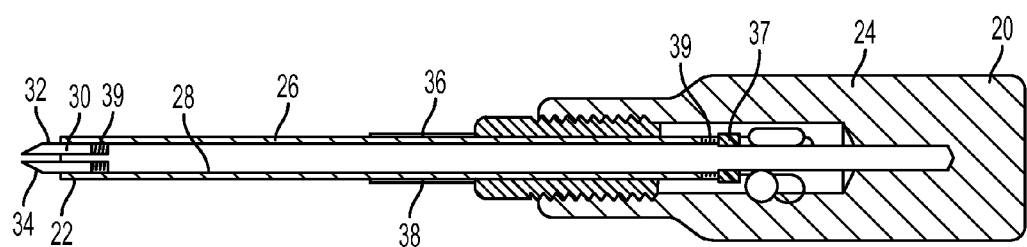
FIG. 2 is a sectional view of the calibration structure of FIG. 1.
Figure 3:
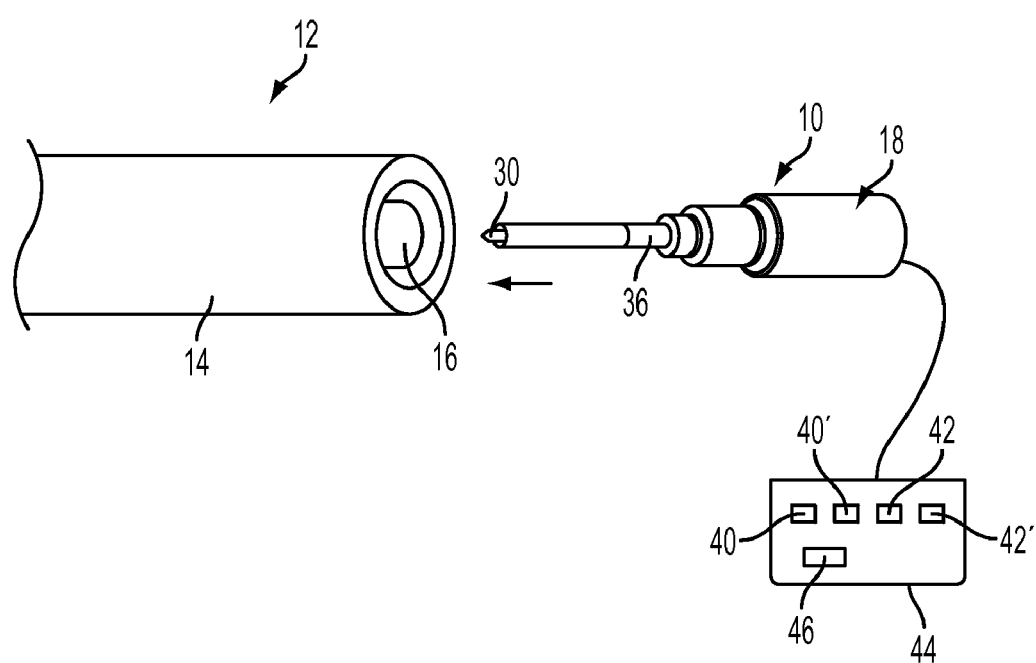
FIG. 3 is a view of the calibration structure of an embodiment, shown ready to be inserted into a flex fuel sensor to calibrate the sensor.

Referring to FIGS. 1 and 2, a mechanical calibration structure or probe is shown, generally indicated at 10, in accordance with the principles of an embodiment thereof. The calibration structure is used for calibrating a flex fuel sensor for a vehicle. As shown in FIG. 3, the flex fuel sensor, generally indicated at 12, has a first sensor electrode 14 and a second sensor electrode 16 and can be of the type described in U.S. Pat. No. 6,842,017 B2, the contents of which is hereby incorporated by reference into this specification. Calibration of the flex fuel sensor 12 using the calibration structure 10 will be explained below.

Returning to FIGS. 1 and 2, the calibration structure includes a body, generally indicated at 18, having a proximal end 20 and a distal end 22. The body 18 includes a first portion at the proximal end 20 defining a handle 24 that is constructed and arranged to be grasped by a user, and a second, elongated portion 26 extending from the handle 24 to the distal end 22. The elongated portion 26 is a plastic tubular member having an inner channel 28.

A first electrode 30 is disposed in the inner channel 28 such that a portion 32 of the first electrode 30 extends outwardly from the end of tubular member at the distal end of the body 18. The portion 32 of the electrode 30 has an outer periphery 34 for contacting the first sensor electrode 14 of the flex fuel sensor 12. A second electrode 36 is disposed about a periphery of the tubular member 26 and is spaced from and electrically insulated from the first electrode 30. The second electrode 36 has an outer periphery 38 that is larger than the outer periphery of the first electrode 30 so as to contact the second sensor electrode 16 of the flex fuel sensor 12. Spring structure 39 (FIG. 2) is preferably provided to bias the first and second electrodes (30, 36) to ensure reliable contact with the first and second sensor electrodes (16, 14), respectively so that the first and second electrodes stay in place and yield the consistent capacitance and/or conductance values intended to be input into the fuel sensor 12 as explained more fully below. A plastic clip 37 is preferably installed to further insulate the first electrode 30 from the second electrode 36.

A capacitor 40, a resistor 42, or a combination of a capacitor with a resistor, of a certain value is electrically connected with the first electrode 30 and the second electrodes 36, by welding, soldering or the like. If only the capacitor 40 of a certain value is used, it represents the capacitance of the test fuel making the calibration structure 10 into a capacitor of a set value. With the capacitor 40 employed, the calibration structure 10 is used to input an exact known capacitance value into the fuel sensor 12 (FIG. 3) and thus is used to calibrate the sensor 12. If only a resistor 42 of a certain value is used, it represents the conductance of the test fuel making the calibration structure into a conductor of a set valve. With the resistor 42 employed, the calibration structure 10 is used to input an exact known conductance value into the fuel sensor 12 (FIG. 3) and thus is used to calibrate the sensor 12. The resistor 42 can be set up in any combination with the capacitor 40 to make a calibration structure that measures both capacitance and conductance. Alternatively, the resistor 42 or capacitor 40 can be configured alone to make only conductance calibration structure or only a capacitance calibration structure, respectively.

Thus, with reference to FIG. 3, the calibration structure 10 can be inserted into the flex fuel sensor 12 with the first and second electrodes (30, 36) electrically contacting with the respective first and second sensor electrodes (16, 14) so as to emulate the test fluid. In other words, the first and second electrodes provide a known input to the flex sensor similar to the known input of a test liquid or fuel. A series of calibration structures 10 with different capacitance and conductance values could be provided to emulate a variety of fuel concentrations and complete a matrix of different values required in the calibration. These calibration structures 10 are thus substituted into the calibration process in lieu of the test liquid or fuel.

As shown FIGS. 1 and 2, the capacitor 40, the resistor 42, or the combination of a capacitor with a resistor, is disposed within the body 18, in particular, within the handle 24 to keep stray capacitance from being introduced by handling. Alternatively, with reference to FIG. 3, a plurality of different value capacitors 40, 40' and different value resistors 42, 42' can be disposed outside of the body 18 and in a separate structure such as a test box 44. Switching structure 46 is provided in the test box 44 or is otherwise associated with the resistors and capacitors to switch between the capacitors, or between the resistors, or between combinations of capacitors with resistors to provide the known input to the flex fuel sensor 12. Such switching can be done manually or automatically via a controller.

Once the flex fuel sensor 12 is properly adjusted and qualified by using the calibration structure 10 and without using a test fluid, the sensor 12 can then be used in the application. Thus, the calibration structure 10 can be used in manufacturing and calibration of a flex fuel sensor. Additional uses include diagnosis of flex fuel sensors in the field, and development of flex fuel software algorithm in a lab.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A calibration structure for calibrating a flex fuel sensor for a vehicle, the flex fuel sensor having a first sensor electrode and a second sensor electrode, the calibration structure comprising:
   a first electrode,
   a second electrode spaced from and electrically insulated from the first electrode, and
   at least one capacitor, or at least one resistor, or at least one combination of a capacitor with a resistor, of a certain value electrically connected with the first and second electrodes,
   wherein the first and second electrodes are separated from the first and second sensor electrodes and wherein the first electrode is constructed and arranged to be moved into contact with the first sensor electrode and the second electrode is constructed and arranged to be moved into contact with the second sensor electrode to provide a known input value to the flex fuel sensor for calibration of the flex fuel sensor without the use of test liquids.

2. The calibration structure of claim 1, wherein the second electrode has an outer, generally cylindrical periphery that is larger than an outer periphery of the first electrode.

3. The calibration structure of claim 1, further comprising a body having proximal and distal ends, the first and second electrodes being associated with the body, the first electrode being disposed generally at the distal end of the body.

4. The calibration structure of claim 3, wherein the body includes a first portion at the proximal end defining a handle constructed and arranged to be grasped by a user, and a second, elongated portion extending from the handle to the distal end.

5. The calibration structure of claim 4, wherein the elongated portion is a tubular member having an inner channel, the first electrode being disposed in the channel such that a portion of the first electrode extends outwardly from the tubular member and the second electrode is disposed about a periphery of the tubular member.

6. The calibration structure of claim 3, wherein the capacitor, the resistor, or the combination of a capacitor with a resistor is disposed within the body.

7. The calibration structure of claim 4, wherein the capacitor, the resistor, or the combination of a capacitor with a resistor is disposed within the handle.

8. The calibration structure of claim 3, wherein the capacitor, the resistor, or the combination of a capacitor with a resistor is disposed outside of the body and in a separate structure.

9. The calibration structure of claim 8, wherein a plurality of different value capacitors and a plurality different value resistors are provided in the separate structure, the calibration structure including switching structure associated with the capacitors and resistors to selectively switch between the capacitors, or between the resistors, or between combinations of the capacitors and resistors, to provide the known input value.

10. The calibration structure of claim 1, further comprising spring structure to bias the first and second electrodes to ensure contact with the first and second sensor electrodes, respectively.

11. The calibration structure of claim 1, in combination with the fuel flex sensor, wherein the first electrode removably contacts the first sensor electrode and the second electrode removably contacts the second sensor electrode.

12. A method of calibrating a flex fuel sensor for a vehicle, the flex fuel sensor having a first sensor electrode and a second sensor electrode, the method comprising:
   providing a calibration structure comprising a first electrode, a second electrode spaced from and electrically insulated from the first electrode, and at least one capacitor, or at least one a resistor, or at least one combination of a capacitor with a resistor, of a certain value electrically connected with the first and second electrodes, and
   moving the calibration structure so that the first electrode makes electrical contact with the first sensor electrode and the second electrode makes electrical contact with the second sensor electrode thereby providing a known input value to the fuel flex sensor for use in calibrating the fuel flex sensor absent the use of test liquids.

13. The method of claim 12, wherein a single capacitor is provided having the certain value that represents a capacitance of a certain test liquid such that the known input value is a capacitance value.

14. The method of claim 12, wherein a single resistor is provided having the certain value that represents a conductance of a certain test liquid such that the known input value is a conductance value.

15. The method of claim 12, further comprising providing a plurality of calibration structures with each calibration structure being constructed and arranged to emulate a known capacitance or conductance value of a test liquid.

16. The method of claim 12, wherein a plurality of different value capacitors and a plurality of different value resistors are provided together with switching structure, the method further comprises:

selectively switching between the capacitors, or between the resistors, or between combinations of the capacitors and resistors, to provide the known input value.

17. The method of claim 12, wherein the step of providing calibration structure includes providing a body having an elongated tubular member, the first electrode having a portion extending from a distal end of the tubular member, the second member being disposed about a periphery of the tubular member.

18. The method of claim 12, further comprising biasing the first and second electrodes as to maintain contact with the respective first and second sensor electrodes.

19. A calibration structure for calibrating a flex fuel sensor for a vehicle, the flex fuel sensor having a first sensor electrode and a second sensor electrode, the calibration structure comprising:

a first electrically conductive member, a second electrically conductive member spaced from and electrically insulated from the first electrically conductive member, and means for providing capacitance, or resistance, or a combination of a capacitance and resistance, of a certain value through the first and second electrically conductive members, wherein the first and second electrically conductive members are separated from the first and second sensor electrodes and wherein the first electrically conductive member is constructed and arranged to be moved into contact with the first sensor electrode and the second electrically conductive member is constructed and arranged to be moved into contact with the second sensor electrode to provide a known input value to the flex fuel sensor for calibration of the flex fuel sensor without the use of test liquids.

20. The calibration structure of claim 19, wherein the means for providing is a separate capacitor, or a separate resistor, or a combination of a separate capacitor and separate resistor, electrically connected with the first and second electrically conductive members.

* * * * *